US00PP16328P3

(12) United States Plant Patent
Morales et al.

(10) Patent No.: US PP16,328 P3
(45) Date of Patent: Mar. 14, 2006

(54) PINEAPPLE PLANT NAMED 'HONEY GOLD'

(50) Latin Name: *Ananas comosus*
Varietal Denomination: Honey Gold

(75) Inventors: Juan Luis Morales, Buenos de Aires de Puntarena (CR); Hans Sauter, San Jose (CR); Thomas R. Young, Coral Gables, FL (US)

(73) Assignee: Del Monte Fresh Produce International Inc., Coral Gables, FL (US)

( * ) Notice: Subject to any disclaimer, the term of this patent is extended or adjusted under 35 U.S.C. 154(b) by 268 days.

(21) Appl. No.: 10/614,447

(22) Filed: Jul. 7, 2003

(65) Prior Publication Data

US 2005/0010978 P1 Jan. 13, 2005

(51) Int. Cl.
*A01H 5/00* (2006.01)

(52) U.S. Cl. ..... Plt./156

(58) Field of Classification Search ..... Plt./156
See application file for complete search history.

(56) References Cited

PUBLICATIONS

The New Royal Horticultural Society Dictionary of Gardening, 1992. The MacMillan Press Limited, London, vol. 1 (A to C), p. 159.*

* cited by examiner

*Primary Examiner*—Anne Marie Grunberg
*Assistant Examiner*—June Hwu
(74) *Attorney, Agent, or Firm*—Dodds and Associates

(57) ABSTRACT

A new pineapple variety named "Honey Gold" is provided. High levels of brix, total sugars, citric acid and ascorbic acid characterize the variety. The new variety bears 0–3 slips.

6 Drawing Sheets

Latin name: *Ananas comosus.*
Variety denomination: 'Honey Gold'.

BACKGROUND OF THE INVENTION

The present invention comprises a new and distinct pineapple variety of *Ananas comosus,* hereinafter referred to by the variety name 'Honey Gold'. The variety has been developed by using clonal selection within the parent population. The process started at the end of 1997 using material from the hybrid Tainung 11 (also known as Perfume pineapple in Taiwan)(non patented). The original seedlings were asexually reproduced using stem cuttings and crowns (asexual seeds). The pineapple plant 'Honey Gold' was developed through mass selection at the research area of Corporacion de Desarrollo Agricola Del Monte, S.A.Pindeco, Buenos Aires-Puntarenas, Costa Rica. The process of mass selection took five years of consecutive plantings and selections.

The main objective of the selection program, was to obtain a pineapple variety with a nice tasting fruit, that would keep the original aroma, with fruit of an appropriate size and shape, but distinguished for having a higher concentration of ascorbic and citric acid, brix or soluble solids, an fewer plant slips, with respect to the parental line.

Personnel in Buenos Aires-Puntarenas, Costa Rica, have developed this new plant. From a group of 19 crowns (asexual seeds) (original parental population) obtained through personnel in Hong Kong, the process of sowing began in Buenos Aires Puntarenas, Costa Rica, by selecting the plants with better characteristics through three generations.

The clone selected after all this effort, resembles the original parental material, but it is distinquished by its higher sugar (TSS), citric acid, ascorbic acid levels, and also by the fewer slips per plant and fewer spines in the leaves.

SUMMARY OF THE INVENTION

The invention relates to a new and distinct variety of the Bromeliaceae, or pineapple family, which was derived by clonal selection from the hybrid Tainung 11, or Perfume pineapple, after continued five year selection and reproduction effort.

The new plant variety is characterized by smooth leaves, with occasional presence of spines on the leaf tips; by the reduced number of slips and the higher citric acid and ascorbic acid levels, and the higher soluble solids content of the fruit flesh, when compared with the parental line. The fruit is cylindrical to conic in shape, of medium size, and very resistant to skin dehydration damage. Mature fruit has an intense yellow color and a strong and sweet aroma, and a wonderful taste, characteristic of the parental line. It is susceptible to chill damage (or internal browning). Even in the absence of refrigeration, the shelf life of the fruit is very long, when compared with other varieties as evidenced by less fruit fermentation, dehydration and brown spots. This new variety produces moderate yields of fruit, best suited for the fresh market.

BOTANICAL DESCRIPTION OF THE PLANT

Figure 1:
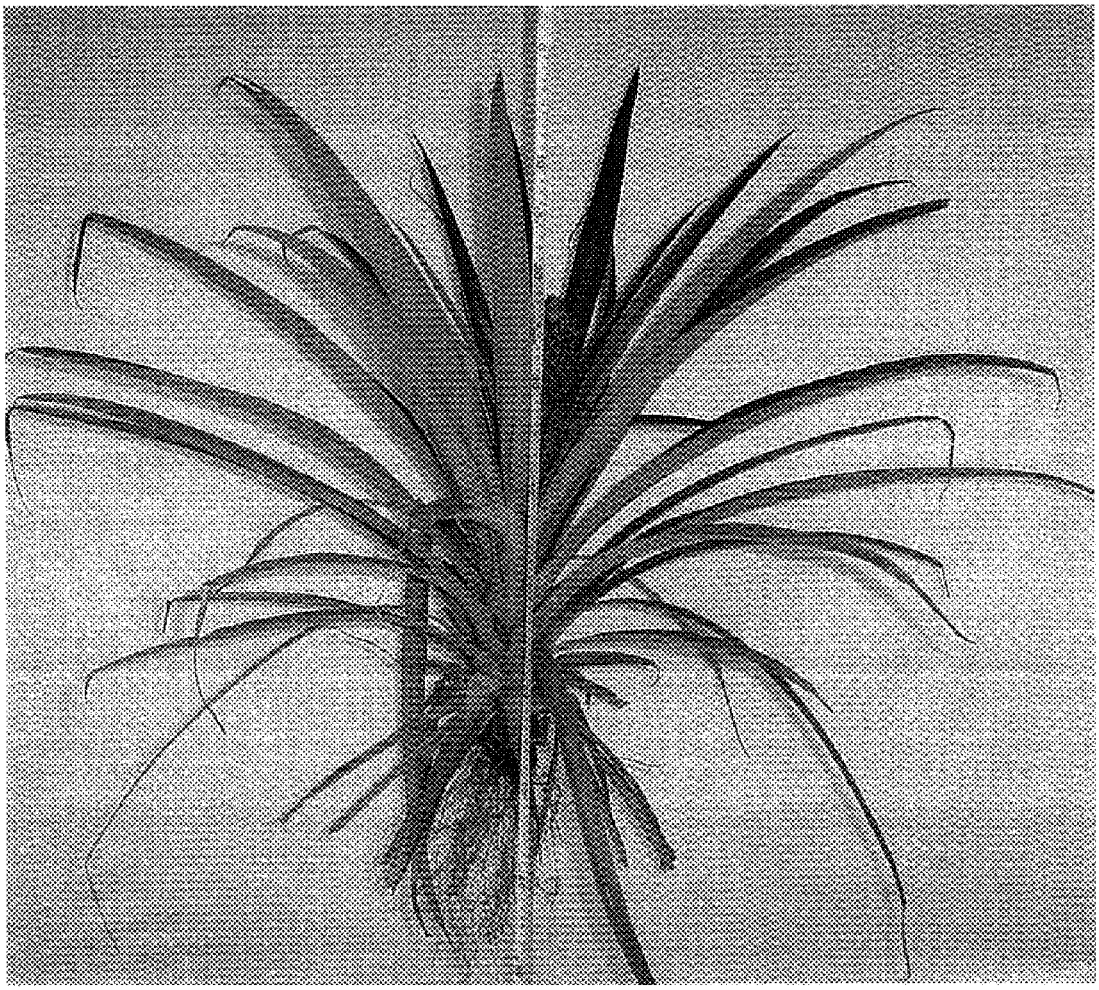
FIG. 1. Shows the lateral view of a plant and root system against a metric ruler.
Figure 2:
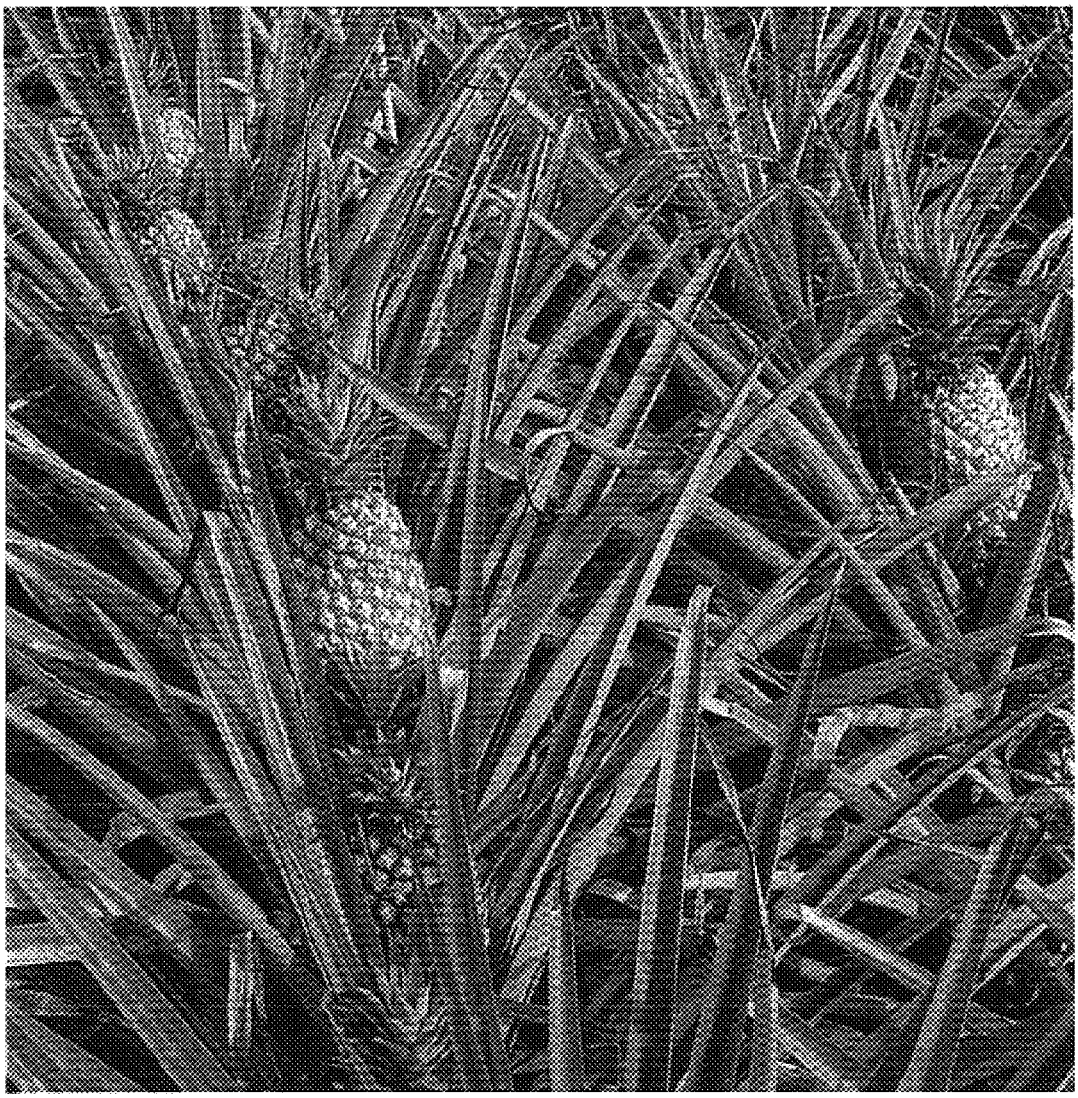
FIG. 2. Shows a 'Honey Gold' plantation.
Figure 3:
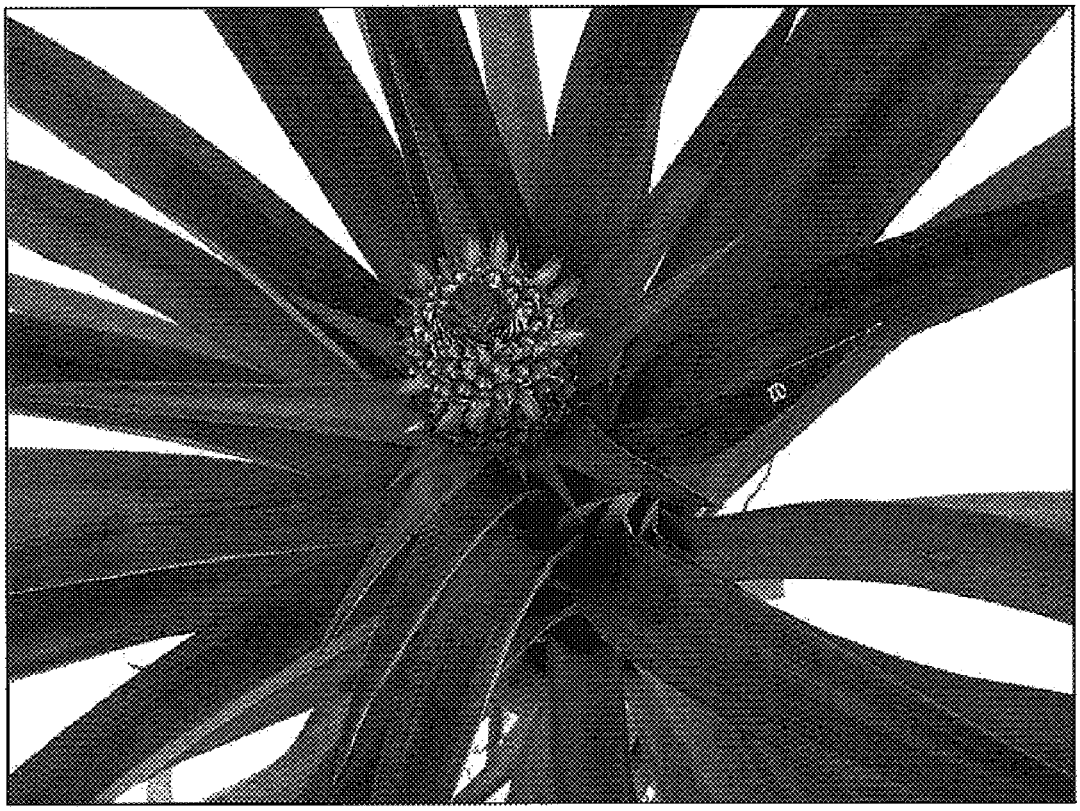
FIG. 3. Shows an overhead view of a 'Honey Gold' plant.
Figure 4:
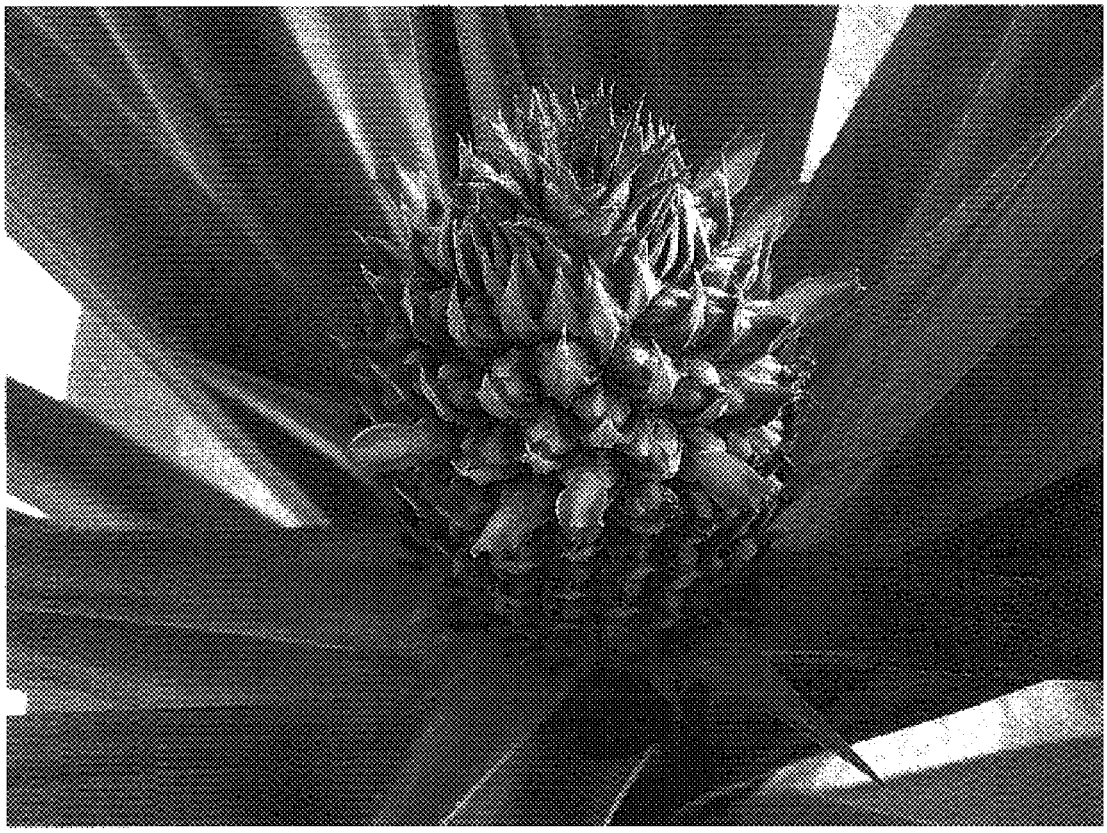
FIG. 4. Shows a close-up of an immature fruit.
Figure 5:
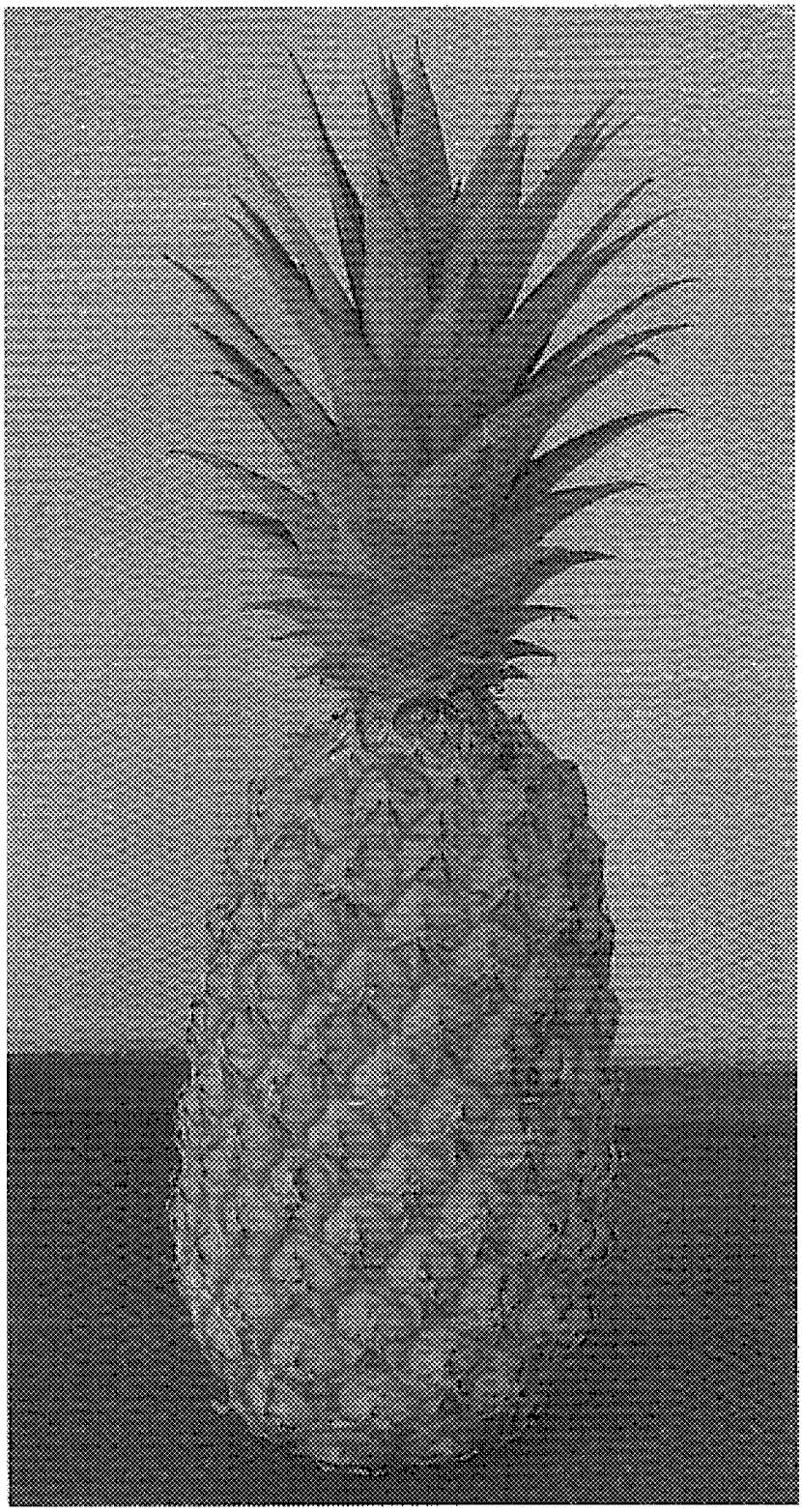
FIG. 5. Shows a close-up of a mature fruit
Figure 6:
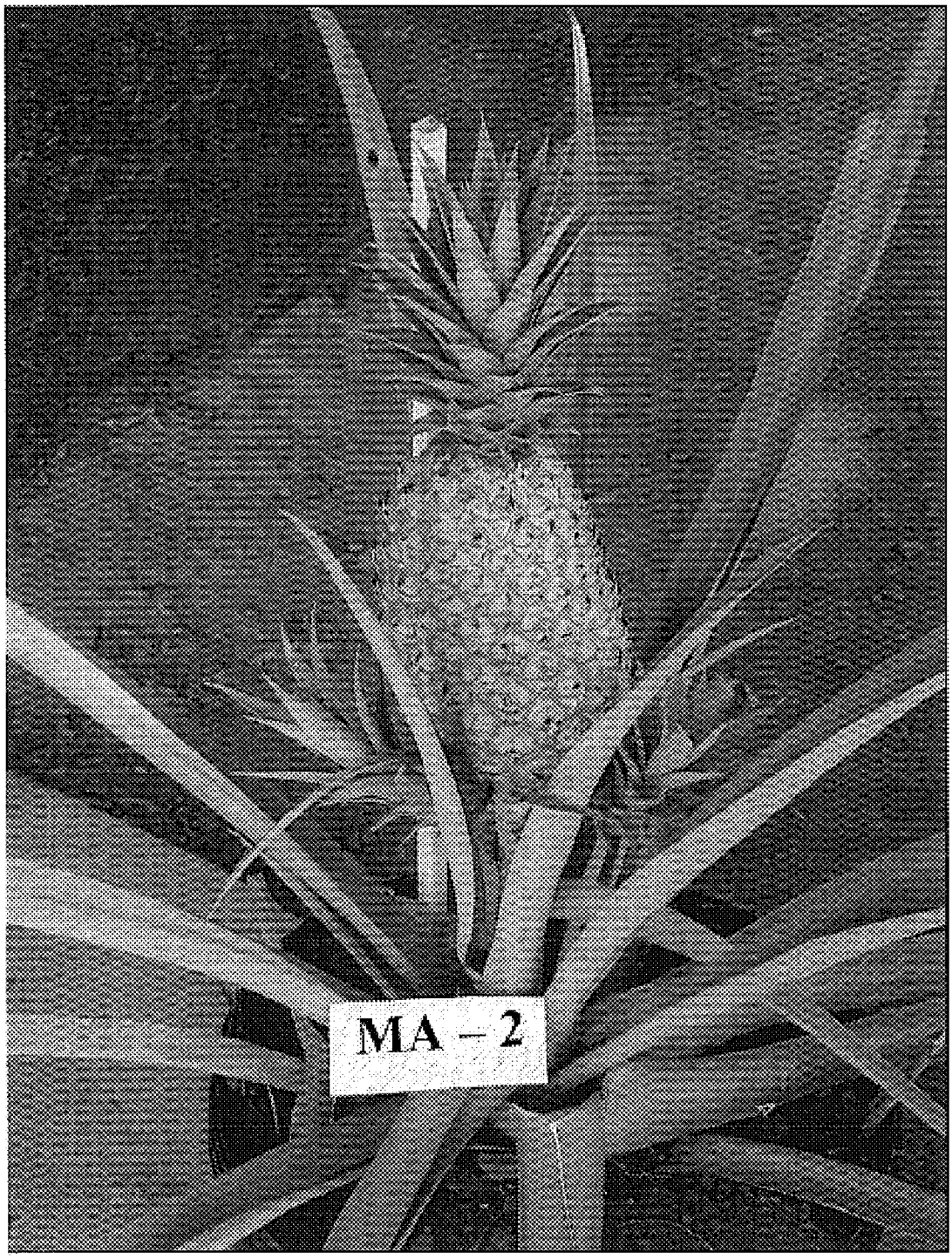
FIG. 6. Shows a mature plant with three or less slips. Age of the plant is 354 days after planting. MA-2 is breeder's number.

The following detailed description of the new variety is based on observations of well fertilized specimens which were grown under field conditions, in the Buenos Aires region, Costa Rica, at 350 msnm, where temperatures generally range form 14° C. to 37° C., and annual rainfall averages 3251 mm.

The plants were grown at a research facility in Buenos Aires-Puntarenas, Costa Rica.

Color terminology and color designations reported herein are in accordance with Munsell Color Notations for plant tissues published by Munsell Color Macbeth, a division of Kollmorgen Corporation, Baltimore, Md., USA.

The following description was taken at harvest beginning of 2003, of the general population of this new variety, which was sowed from asexual seed. The harvest was 354 days after planting.

Plant identification:
Name: *Ananas comosus.*
Parentage: Tainung 11 (Perfume pineapple).
Origin: Clonal selection, through 5 years of consecutive selections and reproductions (three generations).
Classification:
I. Botanic: Bromeliaceae or pineapple family. Subfamily: Bromelioideae. Genus: *Ananas.* Subgenus: *comosus.* Variety: 'Honey Gold'.
II. Commercial: Bromeliad fruit plant.
*Form.*—Terrestrial (in cultivation), with overlapping sessile leaves from a funnel-formed rosette, surrounding a composite inflorescence (during anthesis) and with 0 to 3 slips in the fruit peduncle that initiate before anthesis, and dominant suckers that are produced in the stem and originate subsequent crops.
General description: 'Honey Gold' (Before anthesis).
Stem:
*I. General.*—Short, upright and sheathed by overlapping leaves, each leaf with a dormant axillary bud.
*II. Stem texture.*—Glabrous and fleshy.
*III. Stem size.*—A) Length (above soil level): Usually between 8 and 15.5 cm at anthesis. B) Diameter between 5 and 7.4 cm at soil level at anthesis.
*IV. Stem shape.*—Cylindrical and with a narrower diameter at the distal part.
*V. Stem color.*—7,5 GY 7/1.
Leaves:
*I. General.*—Closely overlapping sessile leaves (formed in acropetal succession) forming a dense rosette, the outline of which in longitudinal section is roughly heart shaped. The number of leaves fluctuates between 28 and 57 with a 5/13 phyllotaxy.
*II. Texture.*—A) Upper epidermal area: Glabrous, semi-rigid and channeled (or concave) except at the leaf tip. C) Lower epidermal area: Finely striated (longitudinally) and appears covered with white layer consisting of scale-like trichomes.
*III. Leaf arrangement.*—Alternate and in rosette shape.
*IV. Leaf margins.*—Plane, with rarely found irregularly spaced small deltoid-cuspidate hooked spines usually located on the distal portions of leaves.
*V. Leaf venation.*—Parallel.
*VI. Leaf shape.*—Leaves are not uniform in shape and vary with the position of the leaf on the stem. The basal or oldest leaves are lanceolate while the base is considerably expanded. There is a noticeable narrowing in width between non-chlorophyllous (basal) and chlorophyllous (or main portion) of the leaves. The longest or most mature leaves are lanceolate in form but the base is without the arcuate expansions of the preceding leaves. The remaining leaves (or center leaves of the plant rosette) are lanceolate in form with no expansion of width into the base.
*VII. Leaf size* (*at anthesis*).—A) Length: Usually between 69 and 85 cm for those leaves originating from the medium part of the stem with a non-chlorophyllous base that usually is between 2.6 and 6.4 cm of length. B) Width: Normally between 4.1 and 6.0 cm in the mid leaf area of the longest leaves. The expanded basal disk usually has a maximum width of 7.5 to 10 cm. C) Thickness: In the longest leaves, usually vary between 1.6 to 2.4 mm at the center of the mid leaf area and decreased laterally between 0.8 and 1.5 mm at the margin, while becoming slightly thinner at the tip. The expanded basal disk at the mid stem area usually has a maximum thickness of 1.5 to 3.8 mm at the center of the blade and tapering laterally toward margins up to 0.36 to 1.28 mm. D) Terminal crown leaves: average size 9.4 cm, number 77; and margin type smooth.
*VIII. Color.*—A) Upper epidermal surface: 1. General: Color is usually dominated by yellowish green, olive green, and reddish green. The color of the basal disk is dominated by a white hue and light yellow. 2. Chlorophyllous basal disk area: Commonly light yellowish (5Y 8/1, 5Y 8/2). 3. Mid leaf area: Commonly olive green (7.5 GY 5/4, 5R 3/4). 4. Leaf tip area: Commonly olive gray (5.0GY 6/4) reddish purple (5.0RP 4/2). B) Lower epidermal area: 1. General: Commonly olive green to grayish olive green with pale white basal disk area. 2. Lower epidermal surface: Scurfy surface that obscures colors commonly light olive green to grayish olive green (7.5GY 8/2, 7.5GY 7/2). C) Color of the terminal crown leaves 5GY 6/4 (predominant) and 2,5 GY 5/3 (secondary).
Inflorescence (at anthesis):
*I. General.*—Flower composite from 80 to 144 fruit-lets borne per inflorescence of a long peduncle of approximately 21.2 cm length at the apical meristem. Individual bisexual flowers that consists of three sepals, six stamens, three stigmas and three carpels. The inflorescence is self-incompatible producing edible fruit parthenocarpically.
*II. Texture.*—Glabrous and fleshy.
*III. Shape.*—Oval with slightly raised flowers with a reddish green hue in the crown. Crown leaves are short and erect at anthesis.
*IV. Size and color.*—Comparable to specimens of *Ananas comosus* L. mer. Petal color 10 YR 8/1 and 5RP 6/4.
*V. Sepal size.*—0.4 cm, color 10 R 7/4.
*VI. Flora bract's length.*—2 cm, serrated margin (with tiny spines); color 2,5 R 7/4.
Fruit (at harvest):
*I. Size.*—Usually has a weight between 433 and 1051 gms with average fruit of 837 gms. Fruit core's diameter: 2.45 cm.
*II. Shape.*—Cylindrical or slightly conic with small and prominent fruitlets. Medium crown with thin and semi-rigid leaves. Average height of the fruit 19–24 cm; diameter of the fruit: basal 8.92 cm; top 8.46 cm.

*III. How borne.*—Fruit develop from the apical meristem of the plant on a long peduncle, usually between 19 and 24 cm length.

*IV. Color.*—A) Shell: Commonly dark green (7.5GY 4/4), olive green (5.0GY 7/6), reddish (5R 3/6) and/or yellow (10YR 7/8). Fruit core color 2.5 Y 8/6. B) Pulp: Usually light yellow (5.0Y 8/4 to 5.0Y 8/2).

*V. Brix.*—Typically between 14.40 and 18.10 degrees, with an average of 16.18.

*VI. Total acid levels.*—Usually between 0.67 and 1.33 gms citric acid/100 ml of juice (average 0.98).

*VII. Vitamin C content.*—Regularly between 14.73 and 37.36 mg/100 ml of juice, with an average of 21.14.

Plant/fruit resistance /susceptibility to pests and diseases: Moderately susceptible to *Fusarium subglutinans.* Table 2 shows a further comparison of pest and disease resistance of pineapple varieties 'Honey Gold', 'Champaka' and 'MD2'.

Others:

*I. Fertility.*—As any other grown up pineapple, this plant is self-compatible. This is the reason why presence of sexual seeds is almost negative. The materials used for planting are slips and the non-commercial fruit crowns.

*II. Vigor.*—It is considered that the plant vigor is similar as to mother plants. It is a slow-growing plant as compared to other types of pineapple like 'Champaka' or the hybrid 'MD-2'.

*III. Yield.*—Each plant estimated yield is 61 tons/ha.

*IV. Market.*—Fruit will be designated to the international fruit market.

*V. Plant use.*—Fruit will be commercialized into the fresh fruit market.

Summary of special characteristics of 'Honey Gold' selection: The 'Honey Gold' plant presents differences, compared to parental line, as follows:

*Plant with fewer slips.*—According to Chan (1995) Tainung 11 plants usually bear 7 slips while 'Honey Gold' plants bear 0–3 slips. Fewer slips reduce contact with the fruit, hence reducing problems caused by leaves rubbing against the fruit, accumulation of organic matter, and the concomitant staining of the fruit base. It also decreases problems of color inconsistency in the fruit that can be caused by the shade from a high number of slips.

The fruit presents higher levels of brix, citric and ascorbic acid than mother plants. As a result of the clonal selection process, the 'Honey Gold' pineapple has citric acid content that is about 112% as compared to 'Tainung 11' and 14.3% higher Brix than 'Tainung 11'. Ascorbic acid levels are about 28.2% over the levels observed in the original population (original selection of 'Tainung 11' plants). 'Honey Gold' variety has also fewer spines in the leaves than Tainung 11. These characteristics of the 'Honey Gold' plant are stable and reproduced true to type in successive generation of asexual reproduction and are shown in Table 1. Table 3 compares the new variety 'Honey Gold' with several other varieties and cultivars; among others is Tainung 11, which is the closest variety.

TABLE 1

Average of inheritance of characteristics in selection material for 'Honey Gold' pineapple. F1 represents baseline data of the first generation grown from the parental line. F2 generation was selected based on characteriscs of vigor, thorniness and number of slips. F3 was selected based on characteristics of vigor, thorniness and number of slips, but also on brix and ascorbic acid. F4 represents 'Honey Gold' as developed from the parental line by mass clonal selection. The plants of F4 generation display stable inheritance of reduced number of slips per plant and a 40% higher ascorbic acid content than the baseline generation.

| Generation | Ascorbic acid mg/100 ml | Citric Acid g/100 ml | Brix | Number of Slips | Fruit Weight (g) |
|---|---|---|---|---|---|
| F1 | 14.8 | 0.77 | 14.15 | 0–10 | 1463 |
| F2 | 14.7 | 0.6 | 15.95 | 0–7 | 999 |
| F3 | 21.2 | 1.0 | 15.60 | 0–3 | 757 |
| F4 | 20.6 | 0.9 | 14.40 | 0–3 | 954 |

Individual plant description: The following is a general description of a new pineapple plant variety that was grown by vegetative propagation (cloning selection) in a nursery in Buenos Aires, Puntarenas, Costa Rica.

*Plant age.*—10 months after initial propagation and 3 months after forcing.

*Plant diameter.*—About 77 cm between opposite leaf tips.

*Plant height.*—79 cm above ground surface.

Stem:

*I) Length.*—12 cm.

*II) Diameter.*—7.0 cm at base.

Leaves:

*I) Number.*—42.

*II) Length.*—75 cm at longest leaves.

*III) Width (largest leaves).*—At mid leaf (max) 5.2 cm; at basal disk area (max) 8.7 cm.

*IV) Thickness.*—1.8 mm along the axis.

*V) Color.*—A) Upper epidermal area — Chlorophyllous area: Commonly olive green (5.0GY 6/4 and 5.GY 5/4) and reddish brown (5R 8/3). B) Upper epidermal area — Non-Chlorophyllous area: Commonly pale white (5Y 8/1). C) Lower epidermal area: Commonly from olive green to grayish olive green (7.5GY 8/2 and 7.5GY 7/2).

Inflorescence:

*General.*—Composite flower with an inflorescence borne from a long peduncle of approximately 13 cm length at the apical meristem. The flower is composed of 136 fruitlets. Petals are white (10YR 8/1) in the proximal part, and pale lilac (5RP6/4) in the distal part.

Comparison of 'Honey Gold' with other pineapple varieties: There are many pineapple varieties grown world wide; however the majority of the varieties are grown for local consumption. By contrast, only two varieties comprise the vast majority of pineapple grown for commercial distribution (either for fresh or canned). These two varieties are 'Champaka' (also known as 'Smooth Cayene') and 'MD2'. A third variety ('CO2') is also only grown for export purposes, but is not widely cultivated. Since 'Honey Gold' will be grown for export to the US, Europe, and other locations, most of the comparison data generated is made versus 'Champaka' and 'MD2'.

Table 2 depicts differences in susceptibility to pests and diseases: 'Honey Gold' and 'Champaka' are less susceptible than 'MD2' to *Thielaviopsis* sp. (common fruit rot) and

*Elarphia* sp. (a moth species). Otherwise, all three varieties are similar in their response to pests and diseases.

TABLE 2

Susceptibility of certain commercial pineapple varieties to pests and diseases.

| Pest and diseases | Pineapple Variety | | |
|---|---|---|---|
| | Honey Gold | MD2 | Champaka |
| *Elaphria* sp. | S | S+ | S |
| Melybug (*Dysmicocus brevipes*) | S | S | S |
| Thecla (*Strymon basilides*) | S | S | S |
| *Thielaviopsis paradoxa* in fruit (T.V) | S | S+ | S |
| *Phytophtora parasitica* | S | S | S |
| *Helicotylenchus* sp. | S | S | S |
| *Meloidegyne* sp. | S | S | S |
| *Pratylenchus* sp. | S | S | S |

(S = susceptible, S+ = very susceptible)

The result in Table 3 show that 'Honey Gold' has a longer shelf life than 'MD2' because color development of the shell is slower and the variety is less affected by cosmetic defects such as dehydration spots, brown spots and fruit fermentation.

TABLE 3

Comparison of some of the post harvest characteristics of 'MD2' vs. Honey Gold.

| | Shell color development* | | | External Appearance (at days after harvest) | | | | | |
|---|---|---|---|---|---|---|---|---|---|
| | | | | Dehydration spot (%) | | Brown Spot (%) | | Fruit Fermentation (%) | |
| | Days after harvest | | | 15 | 21 | 15 | 21 | 15 | 21 |
| Variety | 0 | 15 | 21 | dah** | dah | dah | dah | dah | dah |
| MD2 | 2 | 3.1 | 5.0 | 23.0 | 56.0 | 3.0 | 7.1 | 0 | 9.0 |
| Honey Gold | 2 | 2.9 | 2.8 | 2.5 | 2.1 | 0 | 0 | 0 | 3.5 |

*Shell color was evaluated on a scale of 12–5 with 1 = green, 5 = completely yellow.
**dah = days after harvest Table 4 compares the characteristics of export vs. local varieties. This table also gives comparison between 'Honey Gold' and the closes tvariety Tainung 11. The characteristics of 'Honey Gold' differ from those of other varieties in the following ways:

1. Slips. 'Honey Gold', 'MD2', 'CO2' and 'Red Spanish' have significantly fewer slips than the other varieties.
2. Fruit weight. The fruit weight of 'Honey Gold' tends to be significantly less than that of the other varieties commonly grown commercially for the export markets.
3. Ascorbic acid. The ascorbic acid content of 'Honey Gold' is intermediate between the low ascorbic acid producing varieties ('Champaka' and 'Tainung') and the high ascorbic acid producing varieties ('MD2' and 'CO2').
4. Citric acid. The citric acid content of 'Honey Gold' is clearly the highest among all the varieties for which data is available.
5. Brix. The sugar content (measured as degrees Brix) of 'Honey Gold' is also very high, but almost all pineapple except 'Red Spanish', 'Perola' and 'Queen' have very high brix.
6. Age to forcing. 'Honey Gold' is relatively slow growing, but data is not available for most varieties in the table.
7. Spininess. Presence of spines on leaves is a characteristic that is commonly used to differentiate among pineapple varieties. 'Honey Gold' is among the varieties that rarely have spines. By contrast, spines are common on the leaves of 'Sarawak', 'Mauritius', 'Red Spanish', 'Tainung 11', 'Perola' and 'Queen'.

TABLE 4

Comparative characteristics of several varieties and cultivars of pineapple

| Variety/ | Number of Slips | | Fruit weight (gr0 | | Ascorbic acid (mg/100 ml) | |
|---|---|---|---|---|---|---|
| Cultivar | Average | Range | Average | Range | Average | Range |
| MD-2[1] | 1.2 | 0–3 | 1820 | 1070–2560 | 53.06 | 37.00–69.06 |
| Honey Gold | 1.5 | 0–3 | 1033 | 450–1678 | 21.14 | 14.73–37.36 |
| Champaka F153[2] | 1.1 | | 1710 | 420–3010 | 12.91 | 8.10–17.72 |
| Champaka F152[3] | 1.5 | | 2328 | | | |
| CO-2[4] | | 2–3 | 2059 | 1297–2590 | | 30.8–55.50 |
| Singapore Spanish[5] | | 2–12 | 1000 | | | |
| Sarawak[5] | 0 | | | 2000–4000 | | |
| Mauritius[5] | 0 | | | 500–1500 | | |
| Josephine[6] | | | | 1100–1300 | | |
| Scarlett[6] | | | | 1400–2000 | | |
| Red Spanish[6] | | 1–3 | | 1200–2000 | | |
| Tainung 11[7] | 6.9 | | 991 | 733–1269 | | 10.40–18.50 |
| Imperial[8] | 9.0 | | 1792 | | | |
| Perolera[8] | | 8–10 | 1800 | | | |
| Perolera o | | 10–15 | | 1000–1500 | | |
| Pernambuco[10] | | | | | | |
| Primavera[10] | | 7–10 | 1300 | | | |
| Queen[11] | 4.0 | | | 500–1000 | 26.00 | |

| Variety/ | Citric acid (gr/100 ml) | | Brix | |
|---|---|---|---|---|
| Cultivar | Average | Range | Average | Range |
| MD-2[1] | 0.6 | 0.36–0.84 | 15.05 | 12.9–17.2 |
| Honey Gold | 0.98 | 0.67–1.33 | 16.18 | 14.4–18.1 |
| Champaka F153[2] | 0.72 | 0.54–0.90 | 14.33 | 11.6–17.0 |
| Champaka F152[3] | 0.73 | | 14.97 | |
| CO-2[4] | | 0.42–0.91 | | 15.0–16.7 |
| Singapore Spanish[5] | | 0.50–0.60 | | 10.0–12.0 |
| Sarawak[5] | | 0.30–0.65 | | 14.0–17.0 |
| Mauritius[5] | | 0.40–0.60 | | 15.0–17.0 |
| Josephine[6] | | | | 17.0–22.0 |
| Scarlett[6] | | | | 15.0–18.0 |
| Red Spanish[6] | | | 12 | |
| Tainung 11[7] | 0.50 | 0.40–0.60 | 14 | 13.2–15.1 |
| Imperial[8] | 0.62 | | 15.8 | |
| Perolera[8] | 0.64 | | 13.1 | |

TABLE 4-continued

Comparative characteristics of several varieties and cultivars of pineapple

| | | | |
|---|---|---|---|
| Perolera o | | | 14–16 |
| Pernambuco[10] | | | |
| Primavera[10] | 0.51 | 13 | |
| Queen[11] | 0.56 | | 14–16 |

[1]Pindeco's historical data base and monthly research report April 2001; Bartholomew et al. Pineapple Botany, Production and Uses.
[2]Pindeco's fruit historical data base. Pindeco's forcing plant weithg data base.
[3]Research report PRI No 63. July 1969. Tables 16, 21 and 29.
[4]Plant patent 8,863
[5]Wee, Y. C. 1972. Some common pineapple cultivars of west Malaysia. Malays, Pineapple pp 7–13.
[6]Bartholomew et al. 2003 The Pineapple, Botany, Production and Uses.
[7]Chang, Ching-Chyn, 1995 Tainung No 13 Pineapple. Jour. Agric. Res. China 44(2):287–296.
[8]Pinto da Cunha et al. O abacaxizeiro. Pineapple News Issue No 10 May 2003.
[9]Pinto da Cunha et al. O abacaxizeiro. Py et al. The pineapple Cultivation and uses.

TABLE 4-continued

Comparative characteristics of several varieties and cultivars of pineapple

[10]Pinto da Cunha et al. O abacaxizeiro. Bartholomew et al. The Pineapple Botany, Production and Uses. Del Monte pineapple germplasm collection database.

Literature: Chang, C. C. 1995. Tainung No. 13 pineapple. Jour. Agric. Res. China 44 (3): 287–296. Chang, C. C., Chen-Yung, W. 1997. Pineapple breeding. In: Chang-LinRen (eds.). Proceedings of a Symposium on Enhancing Competitiveness of Fruit Industry. Special Publication No. 38, Taichung District Agricultural Improvement Station, Taichung, Taiwan. Pp 107–122.

What is claimed is:

1. A new and distinct variety of *Ananas comosus* plant named 'Honey Gold' as shown and described herein.

* * * * *